United States Patent [19]

Shaw

[11] 4,010,749
[45] Mar. 8, 1977

[54] METHOD OF DETECTING INFILTRATION OF INFUSED LIQUID BY COMPARING ALTERED SKIN TEMPERATURE WITH SKIN TEMPERATURE IN AREA OF INFILTRATED LIQUID

[76] Inventor: Robert F. Shaw, 135 Willowbrook Drive, Portola Valley, Calif. 94025

[22] Filed: May 9, 1975

[21] Appl. No.: 576,035

[52] U.S. Cl. ............................. 128/214 E; 222/54
[51] Int. Cl.² ................................................ A61M 5/00
[58] Field of Search .......... 128/214 A, 214 E, 2 H, 128/399, 2.05 P, DIG. 13, 402; 222/54

[56] References Cited

UNITED STATES PATENTS

| | | | |
|---|---|---|---|
| 3,142,158 | 7/1964 | Podolsky | 128/214 A X |
| 3,618,602 | 11/1971 | Shaw | 128/214 E |
| 3,628,525 | 12/1971 | Polanyi | 128/2.05 P X |

Primary Examiner—Richard J. Apley
Assistant Examiner—William R. Browne
Attorney, Agent, or Firm—A. C. Smith

[57] ABSTRACT

Perivascular infiltration of liquid being administered to a patient is detected by the method of altering the temperature of a region of the patient's skin adjacent the site of a transcutaneous puncture and providing an output indicative of the difference between the altered skin temperature and the temperature of the infiltrated liquid.

3 Claims, 2 Drawing Figures

FIGURE 2

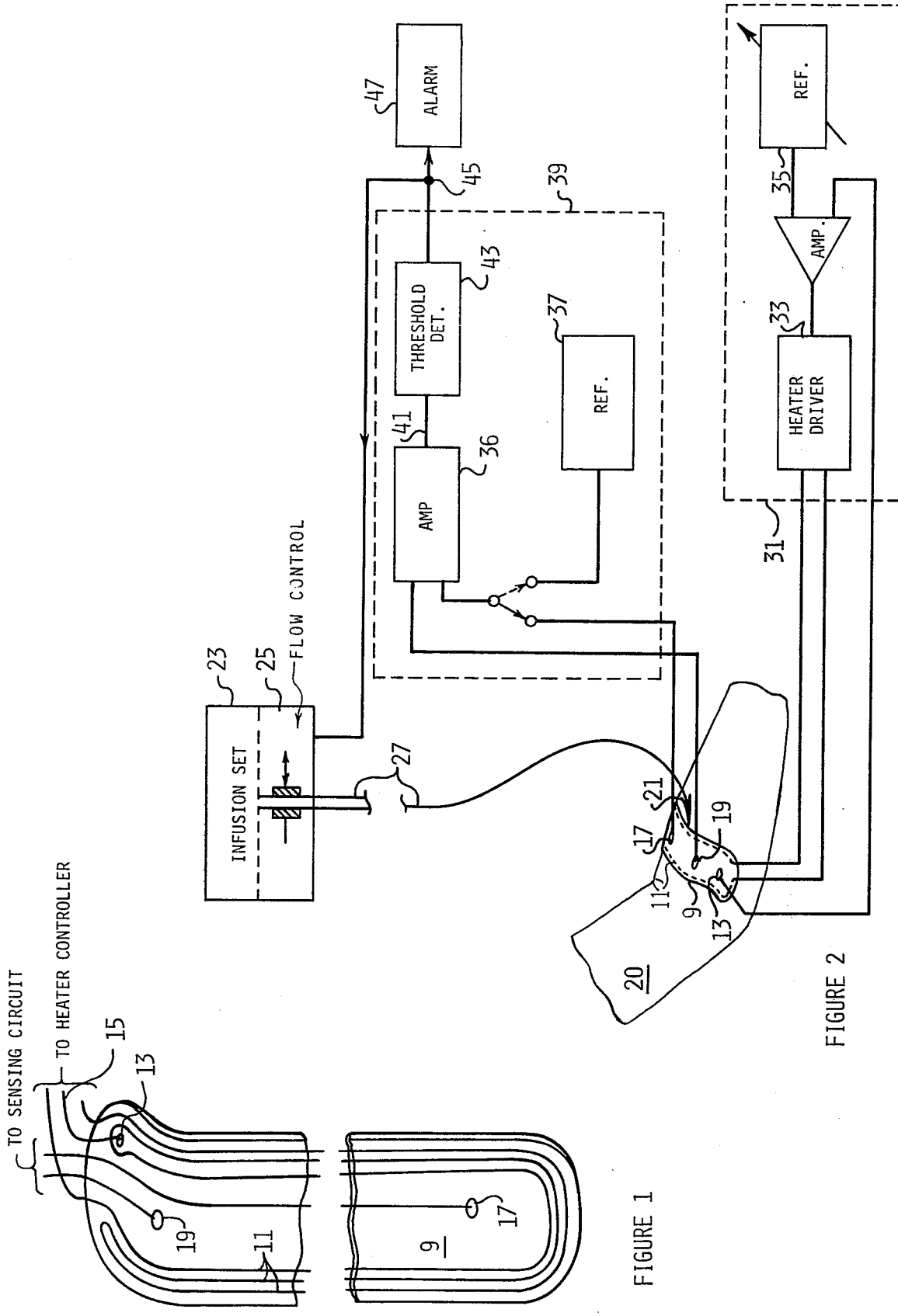

METHOD OF DETECTING INFILTRATION OF INFUSED LIQUID BY COMPARING ALTERED SKIN TEMPERATURE WITH SKIN TEMPERATURE IN AREA OF INFILTRATED LIQUID

BACKGROUND OF THE INVENTION

Intravenous administration of substantial quantities of liquids including water, electrolytes, sugar, blood, pharmaceuticals, and various nutritional materials are commonly administered to hospitalized patients from a glass or plastic container using a plastic tubing conduit which terminates in a needle that is inserted into a superficial vein or artery. A patient's movements, however, may cause the tip of the needle to pierce the vascular wall and cause the liquid being administered to flow in the perivascular tissues. The liquid may accumulate and cause discoloration, discomfort and possible destruction of tissues, while precluding absorption into the metabolic pool of the materials being administered at the selected rate.

Prior liquid infusion infiltration detection apparatus and method (see, for example, U.S. Pat. No. 3,618,602) permitted the early detection of liquid infiltrations so that corrective actions could be promptly instituted. In such prior apparatus and method, the skin temperature in the region overlying the tip of the intravascular needle was continuously monitored. Since liquids administered to a patient are at room temperature or refrigerated, they are typically at a lower temperature than normal skin temperature. Thus, any undesirable perivascular accumulation of administered liquid produces a decrement in skin temperature in the region overlying the accumulation. Since the temperatures of hospital rooms are typically about 20° C.–25° C. and normal skin temperature is typically about 33° C., a significant temperature difference commonly exists between infusion liquid and skin temperature to produce the change in skin temperature that signals the occurrence of an infiltration. However, it has been found in patients who are in a state of shock or who are undergoing, or have recently undergone, substantial surgery or anesthesia and in some small number of other patients, blood flow to the skin may be sufficiently reduced that the patient's skin temperature tends to approximate the ambient temperature. Under these conditions, a substantial difference between skin temperature and the temperature of the liquid being infused is not available to produce a substantial change in the temperature of the skin in a region thereof where perivascular infiltration of the infused liquid occurs. Also, in some circumstances (especially in tropical climates), hospital room temperatures may be elevated to levels approximating normal skin temperatures. Under these circumstances, a substantial temperature difference between skin temperature and the temperature of the liquid being infused is again not available to produce a substantial change in the temperature of the skin in a region thereof where perivascular infiltration of the infused liquid occurs.

SUMMARY OF THE INVENTION

In accordance with the present invention, a surface region of a patient's skin about the site of a transcutaneous puncture into a blood vessel is heated to establish a more reliable thermal difference between the temperature of the patient's skin and the temperature of the liquid being infused. Perivascular infiltration of the infused liquid which may accumulate about the needle tip can thus be detected more reliably, independently of the relative temperatures of the infused liquid and of the patient's skin.

DESCRIPTION OF THE DRAWING

FIG. 1 is a pictorial diagram of the appliance used to regulate the patient's skin surface temperature and to detect changes in skin temperature; and FIG. 2 is a schematic diagram of the illustrated embodiment of the present invention.

DESCRIPTION OF THE PREFERRED EMBODIMENT

Referring now to FIG. 1, there is shown a flexible backing material 9 such as rubber-impregnated nylon, or the like, having a plurality of wires 11 attached thereto to form a heater that may be positioned on, or in close proximity to, a patient's skin, as shown in FIG. 2. A heat-sensitive element 13 such as a thermistor is positioned in close thermal relationship to the heater 11 to provide an output indication on line 15 of the operating temperature thereof. In addition, two sensing thermistors, or other heat-sensitive elements, 17 and 19, are positioned within regions surrounded by the heater 11 to be positioned on, or in close proximity to, the patient's skin for detecting the surface temperature thereof in two separated locations. Thermal conduction between the heater 11 and the sensors 17 and 19 via the backing material should be negligible.

The appliance shown in FIG. 1 including heater 11 and sensors 13, 17 and 19 may be positioned on a patient's skin, as shown in FIG. 2, in the region of the transcutaneous puncture by needle 21 with the thermal sensor 19 positioned on the skin overlying the region of the point of needle 21. In operation, the infusion set 23 may administer a liquid, either by gravity flow or by positive displacement means, via the flow control 25, liquid conduit 27 and the needle 21 which is shown inserted into a blood vessel of a patient 20. The temperature of the liquid being infused is typically at or below room temperature (which, for most hospital rooms, is about 20° C.–25° C., or cooler). Normal skin temperature is generally at or about 33° C., which is substantially different from the temperature of the liquid being infused. However, when patients are in a state of shock or are undergoing, or have recently undergone, surgery or anesthesia or may be subjected to other conditions which substantially diminish skin blood flow, the temperature of the skin drops to approximately the ambient temperature, which is generally cooler, as noted above. In accordance with the present invention, whenever such conditions tend to occur, the local region of the patient's skin surface adjacent the needle 21 is heated to elevate the skin temperature (say, to normal or somewhat above) to assure adequate thermal difference between such local skin temperature and the temperature of the infused liquid. This heating is accomplished by applying electrical signal to the heater 11 from the heater controller 31. A heater driver 33 supplies signal to the heater 11 in response to the error signal that is derived from the combination of signals from the reference supply 35 and the sensor 13. The reference supply 35 may thus be adjusted to set the heater current (and, hence, its temperature) at a selected value. Alternatively, the heater driver 33 may simply supply a selectable current to heater 11 without the aid or benefit of the servocontrol mechanism previously described.

In operation, the two heat sensors 17 and 19 are located within the heated region of the patient's skin surface and normally produce substantial equal output signals. However, in the event the liquid being infused undesirably accumulates about the needle 21 in a perivascular region rather than being properly administered into a blood vessel, the liquid accumulation will alter the skin temperature in the region of sensor 19. The output signal due to this change in temperature may be compared in amplifier 36 with the output signal of sensor 17 or with the output of reference supply 37 of the sensing circuit 39. The reference signal from supply 37 or the output signal from sensor 17 will thus be representative of elevated skin temperature (i.e., about 35° C.–39° C.), independent of the patient's condition. If the amplified difference signal on line 41 exceeds a selected value as determined by threshold detector 43, an output signal is produced on line 45 which may actuate an alarm 47 or actuate the flow controller 25 to terminate further liquid infusion, or both, as described in said U.S. Pat. No. 3,618,602 cited above.

Alternatively, where the room or ambient temperature and the infusion liquid stored under such conditions may be elevated to approximate typical skin temperature, as in tropical regions, or the like, the patient's skin surface temperature in the local region may be decreased below normal skin temperature rather than increased, as previously described, to assure adequate thermal difference between such local skin region and the temperature of the infused liquid. This may be accomplished using electrically-powered Peltier-effect coolers or by circulating refrigerant or by expanding a compressed gas, or the like, in the local region of the skin surface. In this way, the difference between the temperature of the infused liquid and the temperature of the surface skin in the local region may be maintained large for rapid detection of perivascular infiltration of the infused liquid.

I claim:

1. The method of detecting liquid-infusion infiltration into the skin of a patient which is at a temperature not sufficiently different from the temperature of the liquid being infused, the method comprising the steps of:

placing a liquid-delivery conduit into a blood vessel of a patient for delivering an infusion liquid into a blood vessel of the patient;

altering the patient's skin surface temperature relative to the temperature of the liquid in a region of the skin overlying the tip of the intravascular portion of the liquid conduit means; and sensing the difference between the skin surface temperature due to the accumulation of the infused liquid in the perivascular region and the altered skin temperature for providing an output indicative of the difference between the two temperatures.

2. The method according to claim 1 wherein the step of altering the patient's skin surface temperature is accomplished by heating said region of the patient's skin to a temperature above the temperature of the liquid.

3. The method according to claim 1 wherein the step of altering the patient's skin surface temperature is accomplished by cooling said region of the patient's skin to a temperature below the temperature of the liquid.

* * * * *